US00PP37483P2

(12) United States Plant Patent
Kobayashi

(10) Patent No.: US PP37,483 P2
(45) Date of Patent: Jun. 23, 2026

(54) POINSETTIA PLANT NAMED 'Doeuprapre'

(50) Latin Name: ***Euphorbia pulcherrima* Willd.**
Varietal Denomination: Doeuprapre

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 19/065,532

(22) Filed: Feb. 27, 2025

(51) Int. Cl.
*A01H 5/12* (2018.01)
*A01H 6/38* (2018.01)

(52) U.S. Cl.
USPC ..... Plt./307

(58) Field of Classification Search
USPC ..... Plt./303, 307
See application file for complete search history.

(56) References Cited

U.S. PATENT DOCUMENTS

PP32,885 P2 * 3/2021 Kobayashi ..... A01H 5/12
Plt./307

* cited by examiner

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of Poinsettia plant named 'Doeuprapre', characterized by its uniform, upright and mounded plant habit; freely and upright branching habit; dark green-colored leaves; plants flower on or about November 13 in Southern California when grown under natural season conditions; medium to large inflorescences with medium to large smooth dark red-colored flower bracts; and good post-production longevity.

2 Drawing Sheets

Figure 1:
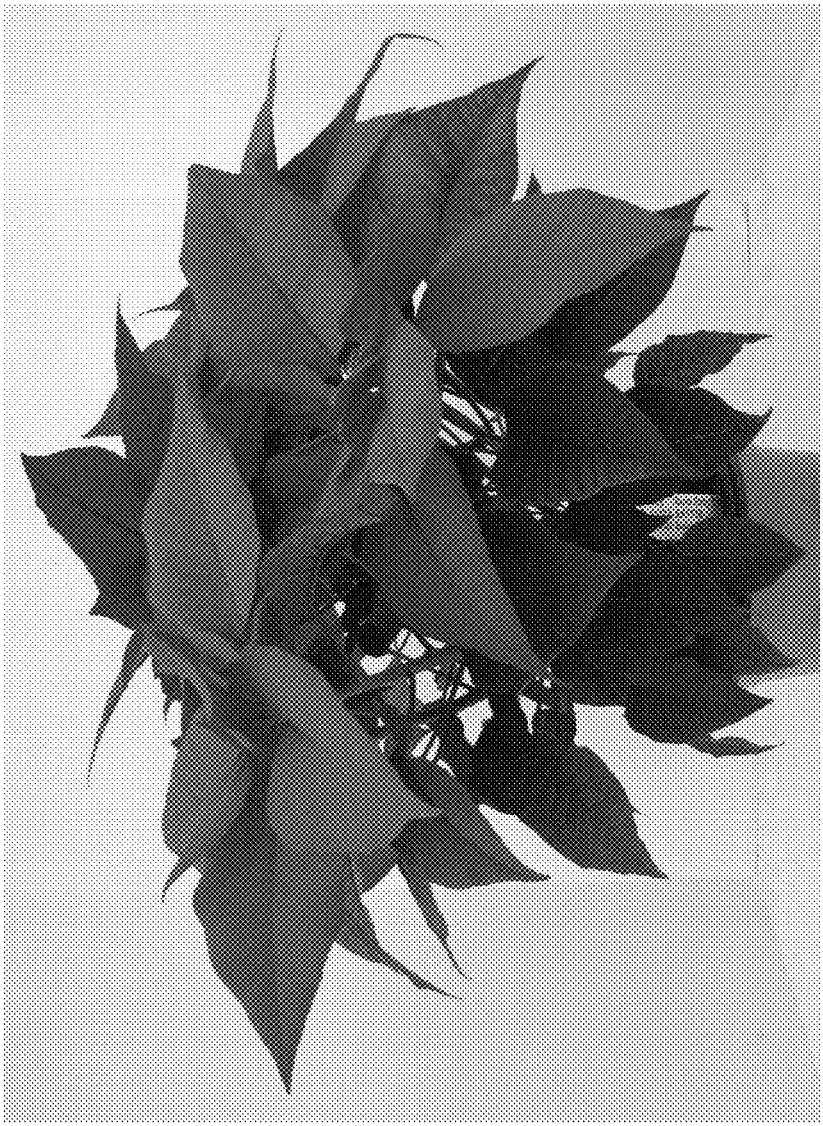

Botanical designation: *Euphorbia pulcherrima* Willd.
Cultivar denomination: 'DOEUPRAPRE'.

BACKGROUND OF THE INVENTION

The present invention relates to a new and distinct cultivar of Poinsettia plant, botanically known as *Euphorbia pulcherrima* Willd., and hereinafter referred to by the cultivar name 'Doeuprapre'.

The new Poinsettia plant is a product of a planned breeding program conducted by the Inventor in Encinitas, California. The objective of the breeding program is to create new uniform and early-flowering Poinsettia plants having large inflorescences with dark red-colored flower bracts and excellent post-production longevity.

The new Poinsettia plant originated from a cross-pollination made by the Inventor in November, 2018 of a proprietary selection of *Euphorbia pulcherrima* Willd. identified as code number EZ13-000100-021 (PE14-21), not patented, as the female, or seed, parent, with a proprietary selection of *Euphorbia pulcherrima* Willd. identified as code number EZ12-000003-001 (PE13-1), not patented, as the male, or pollen, parent. The new Poinsettia plant was discovered and selected by the Inventor as a single flowering plant from within the progeny of the stated cross-pollination in a controlled greenhouse environment in Encinitas, California on Dec. 26, 2019.

Asexual reproduction of the new Poinsettia plant by terminal vegetative cuttings in a controlled greenhouse environment in Encinitas, California since July, 2020 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Doeuprapre'. These characteristics in combination distinguish 'Doeuprapre' as a new and distinct Poinsettia plant:

1. Uniform, upright and mounded plant habit.
2. Freely and upright branching habit.
3. Dark green-colored leaves.
4. Under natural season conditions, plants flower on or about November 13 in Southern California.
5. Medium to large inflorescences with medium to large smooth dark red-colored flower bracts.
6. Good post-production longevity.

In side-by-side comparisons conducted in Encinitas, California, plants of the new Poinsettia differ primarily from plants of the female parent selection in the following characteristics:

1. Plants of the new Poinsettia are not as robust as plants of the female parent selection.
2. Under natural season conditions, plants of the new Poinsettia flower about 19 days earlier than plants of the female parent selection.

3. Plants of the new Poinsettia have broader bracts than plants of the female parent selection.

In side-by-side comparisons conducted in Encinitas, California, plants of the new Poinsettia differ primarily from plants of the male parent selection in the following characteristics:

1. Plants of the new Poinsettia are more robust than and not as compact as plants of the male parent selection.
2. Under natural season conditions, plants of the new Poinsettia flower about two weeks later than plants of the male parent selection.

Plants of the new Poinsettia can be compared to plants of the *Euphorbia pulcherrima* Willd. 'Peterstar', disclosed in U.S. Plant Pat. No. 8,259. In side-by-side comparisons, plants of the new Poinsettia differ primarily from plants of 'Peterstar' in the following characteristics:

1. Leaves of plants of the new Poinsettia are darker green in color than leaves of plants of 'Peterstar'.
2. Under natural season conditions, plants of the new Poinsettia flower about twelve days earlier than plants of 'Peterstar'.
3. Plants of the new Poinsettia have dark red-colored flower bracts whereas plants of 'Peterstar' have bright red-colored flower bracts.

Plants of the new Poinsettia can also be compared to plants of the *Euphorbia pulcherrima* Willd. '490', disclosed in U.S. Plant Pat. No. 7,825. In side-by-side comparisons, plants of the new Poinsettia differ primarily from plants of '490' in the following characteristics:

1. Lateral branches of plants of the new Poinsettia are more upright than lateral branches of plants of '490'.
2. Under natural season conditions, plants of the new Poinsettia flower about five days earlier than plants of '490'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet (FIG. 1) is a side perspective view of a typical flowering plant of 'Doeuprapre' grown in a container.

Figure 2:
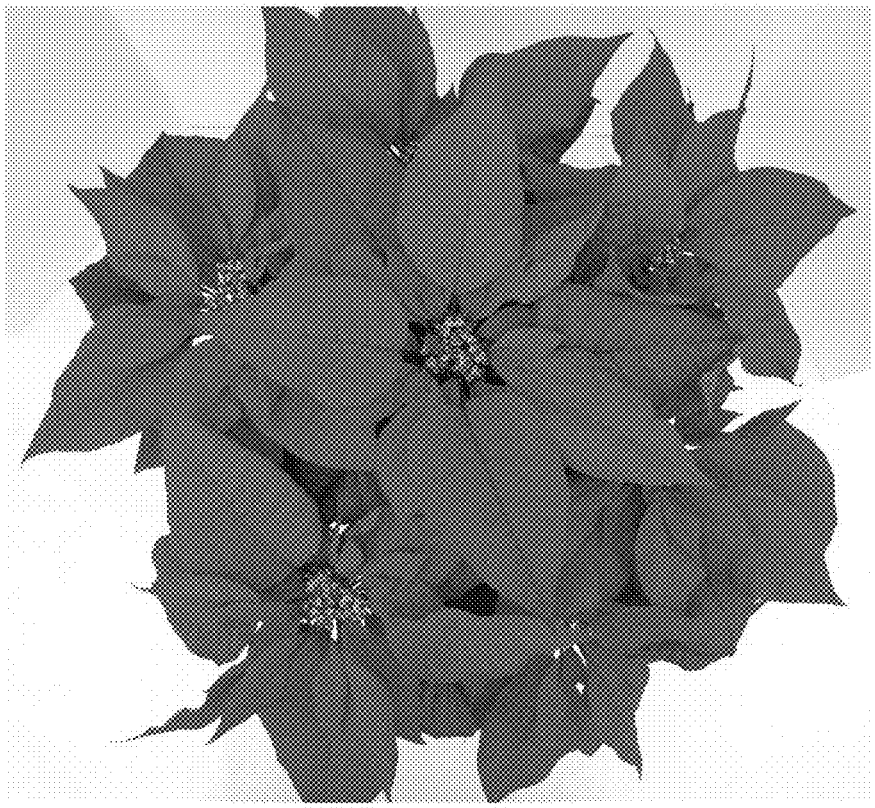

The photograph on the second sheet (FIG. 2) is a top perspective view of a typical flowering plant of 'Doeuprapre' grown in a container.

DETAILED BOTANICAL DESCRIPTION

Plants used in the aforementioned photographs and in the following detailed description were grown during the summer to late autumn in 16.5-cm containers in a polyethylene-covered greenhouse in Encinitas, California under natural season conditions and cultural practices typical of commercial Poinsettia production. During the production of the plants, day temperatures averaged 21° C., night temperatures ranged from 13° to 14° C. and light levels ranged from 3,500 to 4,500 foot-candles. Plants were pinched one time about six weeks after sticking unrooted cuttings and plants were 21 weeks old when the photographs and the description were taken. Measurements and numerical values represent averages for typical flowering plants. In the following description, color references are made to The Royal Horticultural Society Colour Chart, 2015 Edition, except where general terms of ordinary dictionary significance are used.

Botanical classification: *Euphorbia pulcherrima* Willd. 'Doeuprapre'.

Parentage:

*Female, or seed, parent.*—Proprietary selection of *Euphorbia pulcherrima* Willd. identified as code number EZ13-000100-021 (PE14-21), not patented.

*Male, or pollen, parent.*—Proprietary selection of *Euphorbia pulcherrima* Willd. identified as code number EZ12-000003-001 (PE13-1), not patented.

Propagation:

*Type.*—Terminal vegetative cuttings.

*Time to initiate roots.*—About seven to ten days at night temperatures about 20° C. and day temperatures about 27° C.

*Time to produce a rooted young plant.*—About four weeks at night temperatures about 20° C. and day temperatures about 27° C.

*Root description.*—Fibrous; typically white in color, actual color of the roots is dependent on substrate composition, water quality, fertilizer type and formulation, substrate temperature and physiological age of roots.

Plant description:

*Plant and growth habit.*—Uniform, upright and mounded plant habit; inverted triangle; large inflorescences with numerous large flower bracts positioned above the foliar plane.

*Plant height.*—About 42 cm.

*Plant diameter or spread.*—About 58 cm.

*Lateral branch description.*—Quantity: Freely branching habit, about six to seven lateral branches develop after pinching; upright branching habit. Length: About 34 cm. Diameter: Thick, about 1 cm. Internode length: About 1.5 cm to 2 cm. Aspect: About 30° to 40° from vertical. Texture: Smooth, glabrous. Luster: Moderately glossy. Color: Close to 146A.

*Leaf description.*—Arrangement: Alternate, simple. Length: About 12.5 cm. Width: About 9.5 cm to 10.5 cm. Shape: Ovate; occasionally with a single lobe Apex: Acuminate. Base: Truncate with obtuse tendencies. Margin: Mostly entire; occasionally with a single lobe; lobes shallow to medium in depth and divergent; slightly undulate. Aspect: Outwardly to somewhat drooping; moderately carinate. Texture, upper and lower surfaces: Slightly rugose, glabrous; prominent venation on lower surface. Luster, upper surface: Slightly glossy. Luster, lower surface: Matte. Venation pattern: Pinnate, arcuate. Color: Developing and fully expanded leaves, upper surface: Close to N189A; venation, close to 147A. Developing and fully expanded leaves, lower surface: Close to 147A; venation, close to 146A and 146B. Leaf petioles: Length: About 6.5 cm to 7.5 cm. Diameter: About 3.5 mm by 4 mm. Texture, upper and lower surfaces: Smooth, glabrous. Luster, upper and lower surfaces: Moderately glossy. Color, upper surface: Close to 187A to 187B. Color, lower surface: Close to 146A moderately and variably overlain with close to 187A to 187B.

Inflorescence description:

*Inflorescence type and habit.*—Terminal inflorescences are compound corymbs of cyathia with numerous colored flower bracts subtending the cyathia; inflorescences uniformly positioned above the foliar plane.

*Fragrance*.—None detected.

*Flowering response*.—Under natural season conditions, plants typically flower on or about November 13 in Southern California; under artificial long nyctoperiod/short photoperiod conditions, plants flower about seven weeks later.

*Post-production longevity*.—Good post-production longevity; plants of the new Poinsettia maintain good substance and flower bract color for about four to six weeks under interior conditions; flower bracts persistent and cyathia not persistent.

*Inflorescence diameter*.—About 27 cm to 32 cm.

*Inflorescence height* (*depth*).—About 5.5 cm to 7 cm.

*Flower bracts*.—Quantity per inflorescence: Numerous, about 26 to 34. Length, largest bracts: About 13 cm to 14 cm. Width, largest bracts: About 9 cm to 10 cm. Shape: Ovate; occasionally with a single lobe. Apex: Acuminate. Base: Truncate with obtuse tendencies. Margin: Entire; occasionally with a single lobe; lobes shallow to medium in depth and divergent; slightly undulate. Aspect: Mostly horizontal to slightly upright or slightly drooping; moderately carinate. Texture, upper and lower surfaces: Slightly rugose, glabrous; satiny; prominent venation on lower surface. Luster, upper and lower surfaces: Matte. Venation pattern: Pinnate, arcuate. Color: Developing or transitional bracts, upper surface: Ground color, close to 147A; irregular and random sectors, close to N45A. Developing or transitional bracts, lower surface: Ground color, close to 146A and 146B; irregular and random sectors, close to N45A to N45B. Fully expanded bracts, upper surface: Close to N45A. Fully expanded bracts, lower surface: Close to N45B and N45C. Bract petioles: Length: About 4.2 cm to 4.75 cm. Diameter: About 3 mm by 4 mm. Texture, upper and lower surfaces: Smooth, glabrous. Luster, upper and lower surfaces: Moderately glossy. Color, upper surface: Close to 187A to 187B. Color, lower surface: Close to between 144A and 146A moderately and variably overlain with close to 185A.

*Cyathia*.—Quantity per corymb: About 24 to 32. Length: About 9 mm to 10 mm. Width: About 6 mm to 7 mm. Shape: Ovoid. Texture: Smooth, glabrous. Color, inner and outer surfaces: Close to 144A.

*Nectaries*.—Quantity per cyathium: One. Length: About 5.5 mm. Width: About 5 mm. Shape: Roughly deltoid. Texture: Smooth, glabrous. Color, inner and outer surfaces: Close to 144A and distally, close to between 13A and 14A.

*Peduncles*.—Length: About 6 mm to 7 mm. Diameter: About 2 mm to 3 mm. Aspect: Upright to outwardly. Texture: Smooth, glabrous. Luster: Semi-glossy. Color: Close to 144A.

*Reproductive organs*.—Stamens: Quantity per cyathium: About 12 to 16. Filament length: About 5 mm to 7 mm. Filament color: Close to 53A. Anther shape: Round to oval; bi-lobed. Anther length: Less than 1 mm. Anther color: Close to 12A. Amount of pollen: None observed. Pistils: Quantity per cyathium: One; tri-parted. Pistil length: About 8 mm. Stigma shape: Lanceolate, six-parted, recurved. Stigma color: Close to 59A. Style length: About 6 mm. Style color: Close to 59A. Ovary color: Close to 144A to 144B. Fruits & seeds: To date, fruit and seed development has not been observed on plants of the new Poinsettia.

Pathogen & pest resistance: To date, plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'Doeuprapre' as herein illustrated and described.

* * * * *